(12) United States Patent
Wogoman

(10) Patent No.: US 9,402,747 B2
(45) Date of Patent: Aug. 2, 2016

(54) FEMORAL TRIAL COMPONENT

(71) Applicant: DePuy (Ireland), Cork (IE)

(72) Inventor: Thomas E. Wogoman, Warsaw, IN (US)

(73) Assignee: DEPUY (IRELAND), Cork (IE)

( * ) Notice: Subject to any disclaimer, the term of this patent is extended or adjusted under 35 U.S.C. 154(b) by 0 days.

(21) Appl. No.: 14/853,570

(22) Filed: Sep. 14, 2015

(65) Prior Publication Data

US 2016/0000581 A1    Jan. 7, 2016

Related U.S. Application Data

(63) Continuation of application No. 13/731,575, filed on Dec. 31, 2012, now Pat. No. 9,132,011, which is a continuation of application No. 13/530,239, filed on Jun. 22, 2012, now abandoned.

(60) Provisional application No. 61/503,237, filed on Jun. 30, 2011.

(51) Int. Cl.
   *A61F 2/38*   (2006.01)
   *A61F 2/46*   (2006.01)
   *A61F 2/28*   (2006.01)
   *A61F 2/30*   (2006.01)

(52) U.S. Cl.
   CPC .............. *A61F 2/4684* (2013.01); *A61F 2/28* (2013.01); *A61F 2/3859* (2013.01); *A61F 2/46* (2013.01); *A61F 2002/30848* (2013.01)

(58) Field of Classification Search
   CPC combination set(s) only.
   See application file for complete search history.

(56) References Cited

U.S. PATENT DOCUMENTS

| | | |
|---|---|---|
| 4,659,331 A | 4/1987 | Matthews et al. |
| 4,950,297 A | 8/1990 | Elloy et al. |
| 5,306,276 A | 4/1994 | Johnson et al. |
| 5,364,401 A | 11/1994 | Ferrante et al. |
| 5,486,178 A | 1/1996 | Hodge |
| 5,514,143 A | 5/1996 | Bonutti et al. |
| 5,540,696 A | 7/1996 | Booth et al. |
| 5,569,260 A | 10/1996 | Petersen |
| 5,597,379 A | 1/1997 | Haines et al. |
| 5,601,565 A | 2/1997 | Huebner |
| 5,611,802 A | 3/1997 | Samuelson et al. |
| 5,643,272 A | 7/1997 | Haines et al. |
| 5,649,928 A | 7/1997 | Grundei |
| 5,683,469 A | 11/1997 | Johnson et al. |
| 5,704,941 A | 1/1998 | Jacober et al. |

(Continued)

FOREIGN PATENT DOCUMENTS

| | | |
|---|---|---|
| EP | 1 836 997 A1 | 9/2007 |
| EP | 1836997 A1 | 9/2007 |

(Continued)

OTHER PUBLICATIONS

European Search Report, European Application No. 12174182.1-2310, Oct. 2, 2012, 7 pages.

(Continued)

*Primary Examiner* — Sameh Boles
(74) *Attorney, Agent, or Firm* — Barnes & Thornburg LLP

(57) ABSTRACT

An orthopaedic surgical instrument including a femoral trial component configured to be coupled to a surgically-prepared distal end of a patient's femur. The femoral trial component has a fixation side configured to engage a posterior aspect of the surgically-prepared distal femur.

15 Claims, 8 Drawing Sheets

(56) References Cited

U.S. PATENT DOCUMENTS

| | | | |
|---|---|---|---|
| 5,709,689 | A | 1/1998 | Ferrante et al. |
| 5,720,752 | A | 2/1998 | Elliott et al. |
| 5,735,904 | A | 4/1998 | Pappas |
| 5,749,876 | A | 5/1998 | Duvillier et al. |
| 5,769,854 | A | 6/1998 | Bastian et al. |
| 5,788,700 | A | 8/1998 | Morawa et al. |
| 5,860,980 | A | 1/1999 | Axelson et al. |
| 5,935,128 | A | 8/1999 | Carter et al. |
| 6,022,377 | A | 2/2000 | Nuelle et al. |
| 6,024,746 | A | 2/2000 | Katz et al. |
| 6,102,955 | A | 8/2000 | Mendes et al. |
| 6,478,799 | B1 | 11/2002 | Williamson |
| 6,712,824 | B2 | 3/2004 | Millard et al. |
| 7,104,996 | B2 | 9/2006 | Bonutti |
| 7,344,541 | B2 | 3/2008 | Haines et al. |
| 2004/0039450 | A1 | 2/2004 | Griner et al. |
| 2008/0119938 | A1 | 5/2008 | Oh |
| 2008/0140212 | A1 | 6/2008 | Metzger et al. |
| 2008/0147075 | A1 | 6/2008 | Bonutti |
| 2008/0154270 | A1 | 6/2008 | Haines et al. |
| 2008/0269901 | A1 | 10/2008 | Baynham et al. |
| 2009/0076514 | A1 | 3/2009 | Haines |
| 2009/0082773 | A1 | 3/2009 | Haines |
| 2009/0125114 | A1 | 5/2009 | May et al. |
| 2009/0138018 | A1 | 5/2009 | Haines |
| 2009/1025114 | | 5/2009 | May et al. |
| 2010/0082111 | A1* | 4/2010 | Thomas ............... A61F 2/4684 623/20.33 |
| 2010/0125337 | A1 | 5/2010 | Grecco et al. |
| 2010/0298941 | A1 | 11/2010 | Hes et al. |
| 2012/0041566 | A1 | 2/2012 | Lenz et al. |
| 2012/0323334 | A1* | 12/2012 | Jones ................... A61F 2/3859 623/20.35 |
| 2013/0006370 | A1 | 1/2013 | Wogoman et al. |
| 2013/0006371 | A1 | 1/2013 | Wogoman et al. |
| 2013/0006376 | A1 | 1/2013 | Wogoman et al. |
| 2013/0006378 | A1 | 1/2013 | Wogoman |
| 2013/0116795 | A1 | 5/2013 | Wogoman |
| 2013/0144398 | A1 | 6/2013 | Wogoman |

FOREIGN PATENT DOCUMENTS

| | | |
|---|---|---|
| EP | 2168537 | 2/2010 |
| EP | 2 168 537 A1 | 3/2010 |
| EP | 2168537 A1 | 3/2010 |
| WO | 2008/054389 A1 | 5/2008 |
| WO | 2008054389 A1 | 5/2008 |

OTHER PUBLICATIONS

Zimmer NexGen LCCK, Surgical Technique for use with LCCK 4-in-1 Instrument, 2009, 52 pages.
DePuy Orthopaedics, Inc., Sigma Revision and M.B.T. revision Tray, surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev 1, 1999, 74 pages.
PFC Sigma RP-F, Specialist 2 Instruments, Surgical Technique, Performance in Flexion, 2007, 32 pages.
P.F.C. Sigma Rotating Platform Knee System with M.B.T. Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Declaration of Thomas E. Wogoman (with Exhibits A-I), executed Aug. 11, 2014, 145 pages.
United States Patent & Trademark Office, Office Action for U.S. Appl. No. 13/530,239, mailed Sep. 23, 2013, 8 pages.
United States Patent & Trademark Office, Office Action for U.S. Appl. No. 13/530,239, mailed Apr. 1, 2014, 9 pages.
United States Patent & Trademark Office, Office Action for U.S. Appl. No. 13/530,239, mailed Sep. 10, 2014, 10 pages.
United States Patent & Trademark Office, Office Action for U.S. Appl. No. 13/530,771, mailed Jan. 30, 2014, 9 pages.
United States Patent & Trademark Office, Office Action for U.S. Appl. No. 13/754,010, mailed Sep. 23, 2013, 8 pages.
United States Patent & Trademark Office, Office Action for U.S. Appl. No. 13/754,010, mailed Apr. 3, 2014, 7 pages.
United States Patent & Trademark Office, Office Action for U.S. Appl. No. 13/754,010, mailed Sep. 5, 2014, 7 pages.
Second Office Action, State Intellectual property Office, P.R. China, Date of issue: Sep. 14, 2015, 3 pages (English Translation).
GMK Revision, Surgical Technique, Ref. 99.27.12US rev. 1, 1999, 74 pages.
P.F.C. Sigma Rotating Platform Knee System with M.B.T Tray, Primary Procedure with a Curved or Posterior Stablised Implant, 2003, 43 pages.
Extended European Search Report from EP12174182.1, Oct. 2, 2012, 7 pages.

* cited by examiner

FEMORAL TRIAL COMPONENT

This application claims priority under 35 U.S.C. §120 to U.S. patent application Ser. No. 13/731,575, which was filed on Dec. 31, 2012 and which claimed priority under 35 U.S.C. §120 to U.S. patent application Ser. No. 13/530,239, which was filed on Jun. 22, 2012 and which claimed priority under 35 U.S.C. §119 to U.S. Patent Application No. 61/503,237, which was filed on Jun. 30, 2011. Each of these applications are incorporated herein by reference.

TECHNICAL FIELD

The present disclosure relates generally to orthopaedic surgical instruments and, more particularly, to surgical instruments used on a patient's femur.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Femoral components are designed to be attached to a surgically-prepared distal end of a patient's femur. Tibial trays are designed to be attached to a surgically-prepared proximal end of a patient's tibia.

To facilitate the replacement of the natural joint with the knee prosthesis, orthopaedic surgeons use a variety of orthopaedic surgical instruments such as, for example, prosthetic trial components, cutting blocks, drill guides, milling guides, and other surgical instruments. Prosthetic trial components, such as, for example, a femoral trial component and a tibial bearing trial component, are used to size and select the components of the knee prosthesis that will replace the patient's natural joint. A procedure that utilizes the trial components to size and select the components of the knee prosthesis is often referred to as a trial reduction.

SUMMARY

According to one aspect of the disclosure, an orthopaedic surgical instrument includes a polymeric femoral trial component configured to be coupled to a surgically-prepared distal end of a patient's femur. The femoral trial component includes an articular side having a posterior femoral condyle surface and a fixation side that is opposite the articular side. The fixation side has a plurality of ribs that extend in a direction away from the articular side so as to define a plurality of pockets therebetween. Each rib has an outer surface, and the outer surfaces of the ribs define a posterior fixation surface that extends generally in the superior/inferior direction and is configured to match the surgically-prepared distal end of the patient's femur. The femoral trial component also includes a plurality of teeth extending from the posterior fixation surface in a direction away from the articular side. Each tooth of the plurality of teeth has a pointed tip that defines a longitudinal axis of the tooth extending in the medial/lateral direction.

In some embodiments, each tooth of the plurality of teeth may have a triangular cross-section. In some embodiments, the plurality of teeth may include at least four teeth.

Additionally, in some embodiments, the polymeric femoral trial component may be formed as a molded integral component. In some embodiments, the outer surfaces of a number of the plurality of ribs may further define a distal fixation surface extending generally in the anterior/posterior direction and a posterior-chamfer fixation surface extending superiorly and posteriorly from the distal fixation surface to the posterior fixation surface.

In some embodiments, a second plurality of pockets may be defined in each of the distal fixation surface and the posterior-chamfer fixation surface between the plurality of ribs. In some embodiments, the femoral trial component may have an aperture defined in the distal fixation surface, and the aperture may extend from the fixation side to the articular side.

Additionally, in some embodiments, the femoral trial component may further include a lateral posterior condyle including the articular side and the fixation side that is opposite the articular side, and a medial posterior condyle. The medial posterior condyle may include a second articular side including a second posterior femoral condyle surface and a second fixation side that is opposite the second articular side. The second fixation side may have a second plurality of ribs that extend in a direction away from the second articular side so as to define a second plurality of pockets therebetween. Each rib may have an outer surface and the outer surfaces of the ribs may define a second posterior fixation surface that extends generally in the superior/inferior direction and is configured to match the surgically-prepared distal end of the patient's femur. The medial posterior condyle may also include a second plurality of teeth extending from the posterior fixation surface in a direction away from the second articular side.

In some embodiments, the femoral trial component may further have a medial side and a lateral side. The medial side may have at least one notch defined therein extending from the fixation side to the articular side, and the lateral side may have at least one notch defined therein extending from the fixation side to the articular side.

In some embodiments, the medial side may include two notches, and the lateral side may include two notches.

According to another aspect, an orthopaedic surgical instrument includes a polymeric femoral trial component configured to be coupled to a surgically-prepared distal end of a patient's femur. The femoral trial component includes an articular side having a posterior femoral condyle surface and a fixation side that is opposite the articular side. The fixation side has a planar posterior fixation surface that extends generally in the superior/inferior direction and is configured to match the surgically-prepared distal end of the patient's femur. A plurality of teeth extend from the planar posterior fixation surface in a direction away from the articular side. Each tooth has a pointed tip that defines a longitudinal axis of the tooth extending in the medial/lateral direction.

In some embodiments, a plurality of pockets may be defined in the planar posterior fixation surface between the plurality of teeth.

According to another aspect, an orthopaedic surgical instrument includes a polymeric femoral trial component configured to be coupled to a surgically-prepared distal end of a patient's femur. The femoral trial component has a medial side, a lateral side, an articular side including a posterior femoral condyle surface, and a fixation side that is opposite the articular side. The fixation side is configured to engage a posterior aspect of the surgically-prepared distal femur. The polymeric femoral trial component also includes a first notch extending from the fixation side to the articular side that is defined in the medial side, and a second notch extending from the fixation side to the articular side that is defined in the lateral side.

In some embodiments, the fixation side may include a plurality of ribs. Each rib may have an outer surface and the outer surfaces may define a posterior fixation surface extending generally in the superior/inferior direction that is configured to match the surgically-prepared distal end of the patient's femur. A plurality of teeth may extend from the posterior fixation surface in a direction away from the articular side. In some embodiments, the plurality of teeth may include at least four teeth.

Additionally, in some embodiments, each tooth of the plurality of teeth may have a pointed tip that defines a longitudinal axis of the tooth extending in the medial/lateral direction. In some embodiments, the femoral trial component may be formed as a molded integral component. In some embodiments, each tooth of the plurality of teeth may have a triangular cross-section.

BRIEF DESCRIPTION OF THE DRAWINGS

The detailed description particularly refers to the following figures, in which.

DETAILED DESCRIPTION OF THE DRAWINGS

Figure 1:
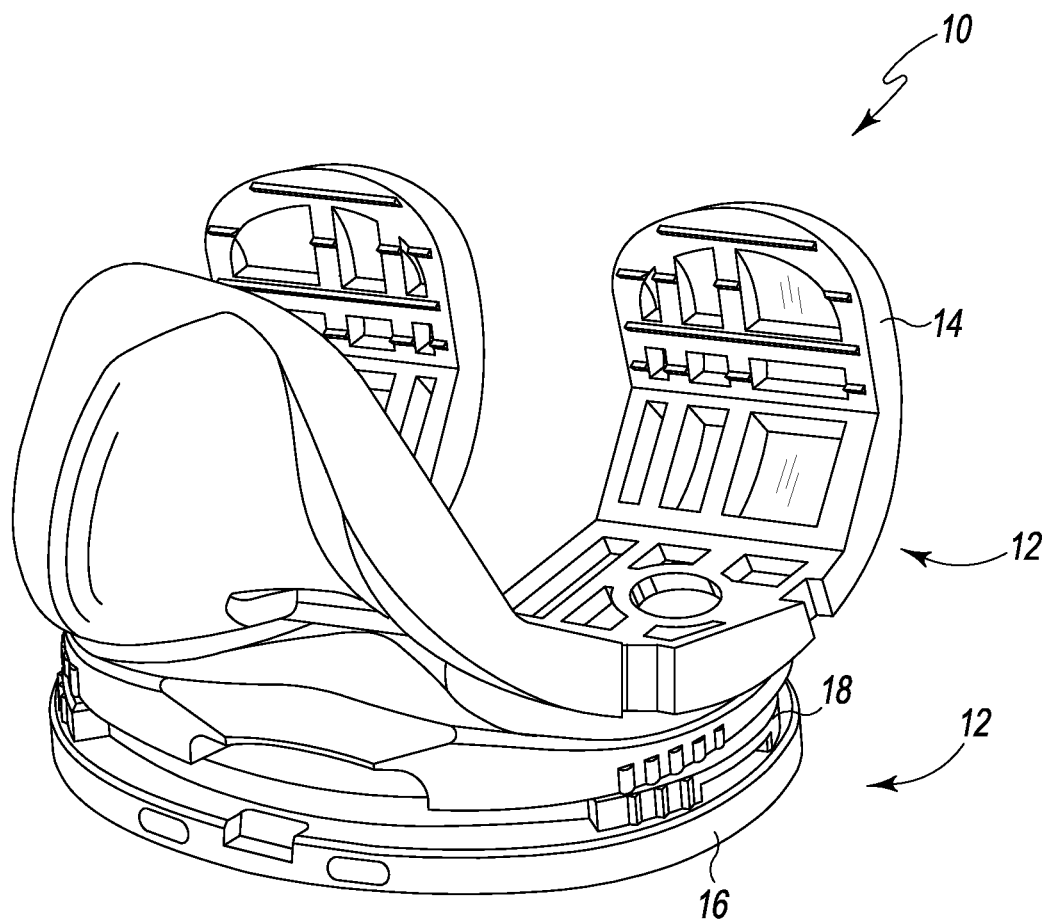
FIG. 1 is a perspective view of an orthopaedic surgical instrument assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIGS. 1-4, an orthopaedic surgical instrument assembly 10 is shown. The orthopaedic surgical instrument assembly 10 has a number of trial components 12, including a femoral trial 14, a tibial base trial 16, and a tibial bearing trial 18. The femoral trial 14 is configured to be secured to a surgically-prepared end of a patient's distal femur 20 (see FIG. 6), whereas the tibial base trial 16 is configured to be secured to a surgically-prepared end of a patient's proximal tibia 22 (see FIG. 8).

Figure 2:
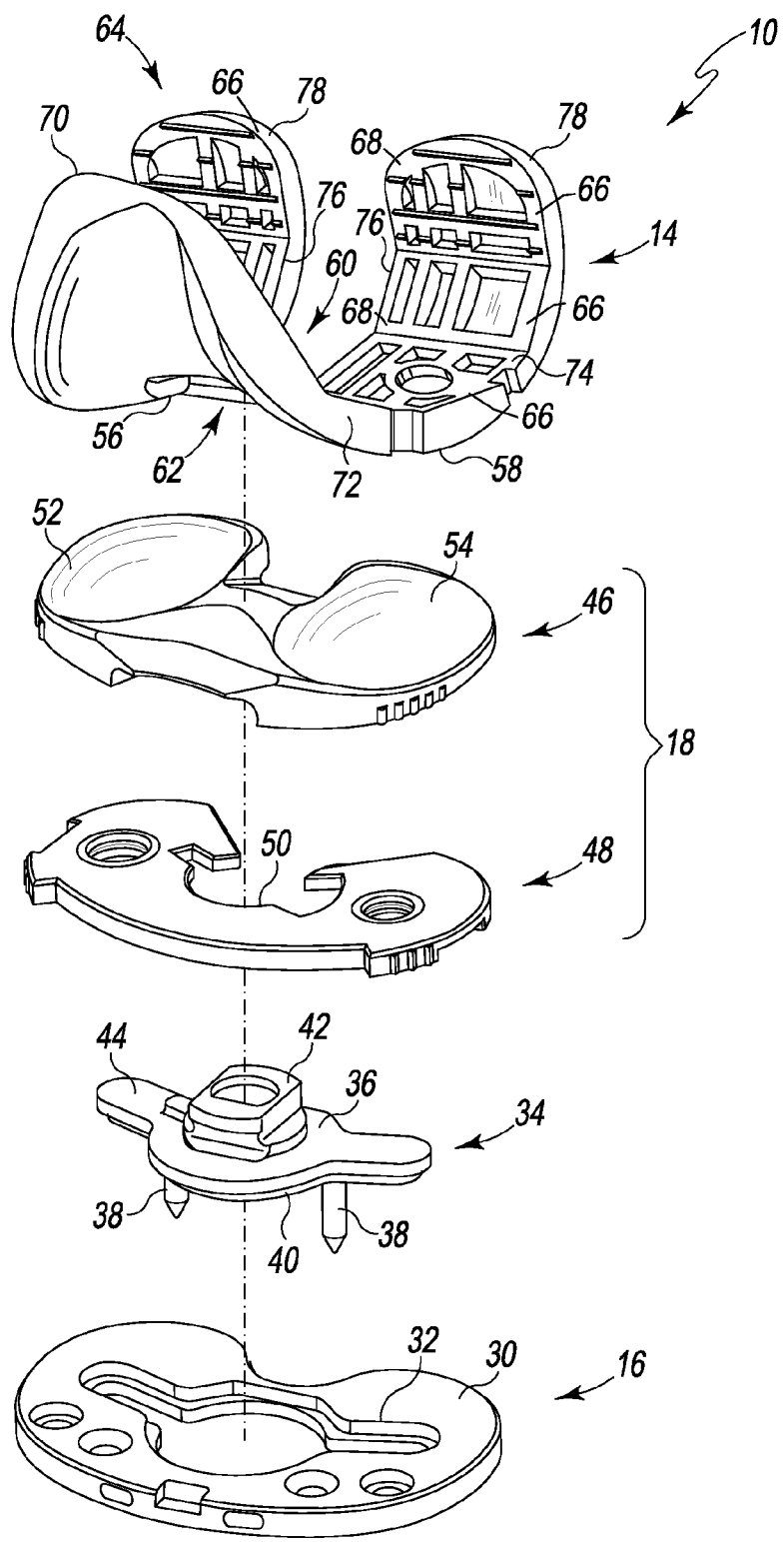
FIG. 2 is an exploded perspective view of the orthopaedic surgical instrument assembly of FIG. 1.

As shown in FIG. 2, the tibial base trial 16 includes a plate 30 having an opening 32 defined therein sized to receive a base insert 34. The base insert 34 includes a body 36 having a number of fixation pins 38 extending away from a lower surface 40 of the body 36. The base insert 34 also includes a post 42 extending away from an upper surface 44 of the body 36. It should be appreciated that in other embodiments the fixation pins 38 may be omitted from base insert 34 or additional fixation pins 38 may be added.

The tibial bearing trial 18 is configured to assist the surgeon in selecting a prosthetic tibial bearing component of a typical knee prosthesis. The tibial bearing trial 18 is a multi-piece assembly that includes a bearing surface trial 46 and a shim 48. The post 42 of the base insert 34 is received in an opening 50 defined in the shim 48 and an opening (not shown) defined in the lower surface of the bearing surface trial 46. The bearing surface trial 46 includes a lateral articular surface 52 and a medial articular surface 54 positioned opposite the lower surface. In the illustrative embodiment, the bearing surface trial 46 is embodied as a fixed bearing trial and is fixed relative to the tibial base trial 16 (i.e., it is configured to not substantially rotate or move in the anterior/posterior direction or medial/lateral direction). In other embodiments, the bearing surface trial 46 may be a mobile bearing trial configured to rotate relative to the tibial base trial 16. As shown in the illustrative embodiment, the tibial bearing trial 18 is a multi-piece assembly, but it should be appreciated that in other embodiments the tibial bearing trial 18 may be a single monolithic component. One example of a tibial bearing trial 18 is shown and described in co-pending U.S. Patent Application Ser. No. 61/503,300, entitled "TRIALING SYSTEM FOR A KNEE PROSTHESIS AND METHOD OF USE" by Thomas E. Wogoman et al., which is incorporated herein by reference.

The femoral trial 14 of the orthopaedic surgical instrument assembly 10 is configured to assist the surgeon in selecting a femoral prosthetic component, which will emulate the configuration of the patient's natural femoral condyles. As such, the femoral trial 14 includes a lateral condyle surface 56 and a medial condyle surface 58, which may be shaped (i.e., curved) in a manner that approximates the condyles of the natural femur. The lateral condyle surface 56 and the medial condyle surface 58 are spaced apart from one another, thereby defining an intercondylar notch 60 therebetween. The articular surfaces 52, 54 of the tibial bearing trial 18 are configured to rotate with the lateral condyle surface 56 and the medial condyle surface 58, respectively, of the femoral trial 14.

Figure 3:
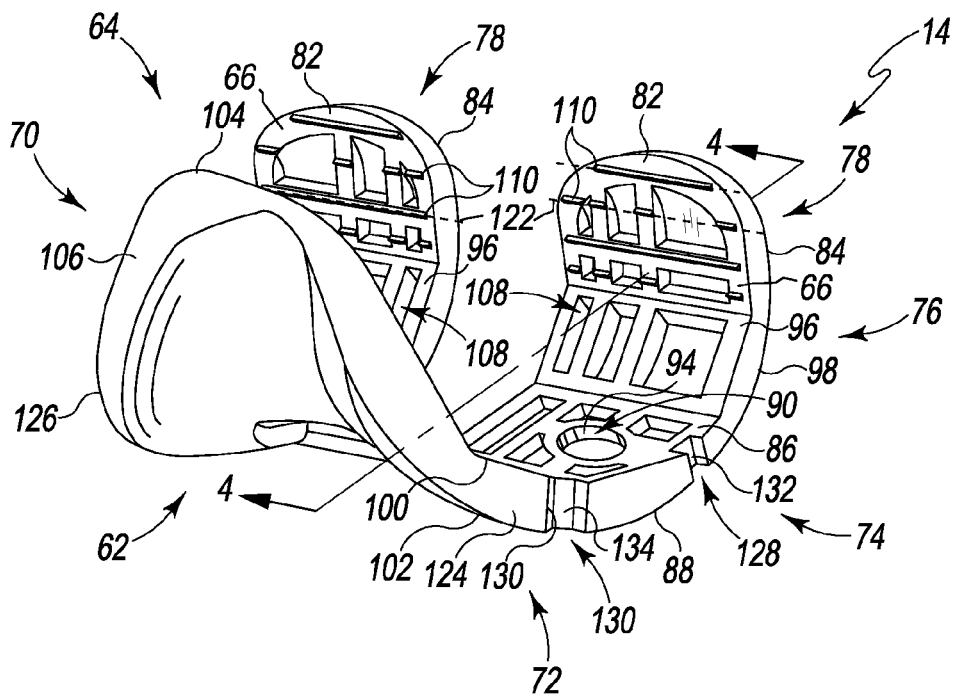
FIG. 3 is a perspective view of the femoral trial component of the orthopaedic surgical instrument assembly of FIG. 1.

As shown in FIG. 3, the lateral condyle surface 56 and the medial condyle surface 58 are formed in an articular side 62 of the femoral trial 14. A fixation side 64, which is the side of the femoral trial 14 that contacts the surgically-prepared distal femur of the patient, is opposite the articular side 62. The fixation side 64 includes a plurality of ribs 66 that extend in a direction away from the articular side 62. Each of the ribs 66 includes an outer surface 68, and the outer surfaces 68 of the ribs 66 cooperate to define multiple surfaces of the fixation side 64. Those surfaces, identified below as "fixation surfaces," mate or match with planar surfaces surgically cut into the patient's femur, as discussed in greater detail below.

Although the femoral trial 14 is illustratively shown as a single integral or monolithic component, the trial 14 is characterized herein by a number of "regions" or "structures." For example, the anterior structure of the femoral trial 14 is referred to herein as an anterior flange 70. Moving along the femoral trial 14 from an anterior to posterior, the anterior flange 70 transitions to an anterior-chamfer region 72, which transitions to a distal condylar region 74. The distal condylar region 74 transitions to a posterior-chamfer region 76. A pair of femoral condyles 78 forms the posterior structure of the femoral trial 14. One of the femoral condyles 78 is medially positioned and the other laterally positioned when the femoral trial 14 is attached to the distal end of the patient's resected femur 20 depending on which knee is being replaced.

Figure 4:
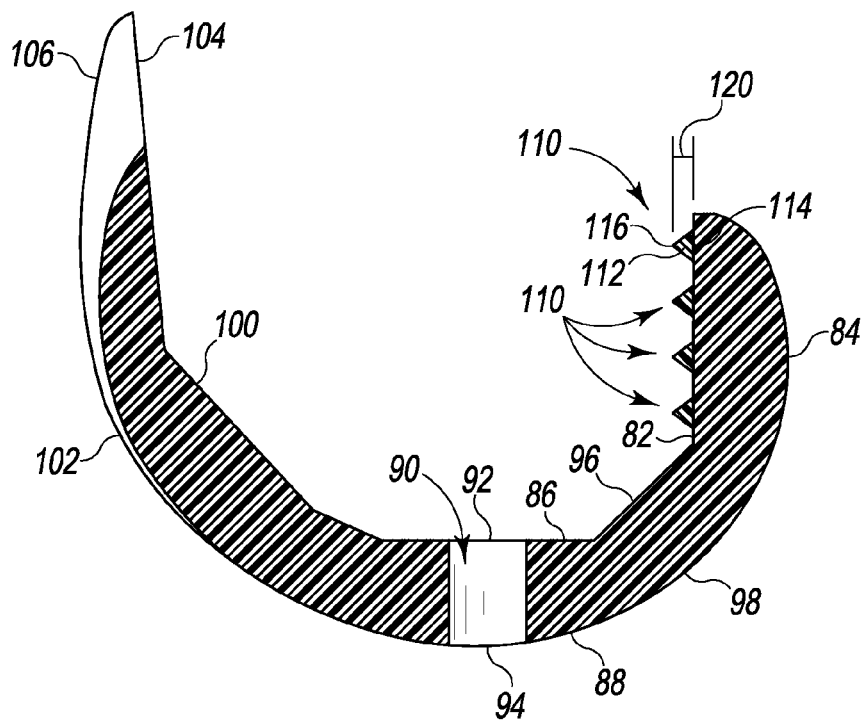
FIG. 4 is a sagittal cross sectional view of the femoral trial component of FIGS. 1-3.

The outer surfaces 68 of the ribs 66 of each of the posterior femoral condyles 78 define a planar posterior fixation surface 82 on the fixation side 64, with one of the posterior fixation surfaces 82 being the lateral fixation surface and the other medial fixation surface. Each posterior fixation surface 82 is positioned opposite a posterior condyle surface 84 on the articulation side 60. As shown in FIG. 4, the posterior fixation surfaces 82 and the posterior condyle surfaces 84 extend generally in the superior/inferior direction.

The outer surfaces 68 of the ribs 66 of the distal condylar region 74 define a pair of planar distal fixation surfaces 86 (one being medially positioned, the other laterally positioned). Each of the distal fixation surfaces 86 is opposite a distal condyle surface 88. As shown in FIG. 3, the distal fixation surfaces 86 extend generally in the anterior/posterior direction.

The distal condylar region 74 also includes a pair of apertures or through-holes 90, one of which is positioned laterally while the other is positioned medially. Each through-hole 90 extends from an opening 92 defined in one of the distal fixation surfaces 86 to an opening 94 defined in the corresponding distal condyle surface 88. Each through-hole 90 is sized to receive a surgical drill, as described in greater detail below.

The posterior-chamfer region 76 of the femoral trial 14 includes a pair of planar posterior-chamfer fixation surfaces 96 defined by the outer surfaces 68 of the ribs 66, with one being medially positioned and the other laterally positioned. The lateral and medial posterior-chamfer fixation surfaces 96 extend superiorly and posteriorly from their respective lateral and medial distal fixation surfaces 86 to their respective posterior fixation surfaces 82. Each of the posterior-chamfer fixation surfaces 96 is positioned opposite a posterior-chamfer condyle surface 98.

Similarly, the anterior-chamfer region 72 includes a pair of planar anterior-chamfer fixation surfaces 100. Each anterior-chamfer fixation surface 100 is positioned opposite an anterior-chamfer condyle surface 102. The anterior-chamfer fixation surfaces 100 extend superiorly and anteriorly away from their respective lateral and medial distal fixation surfaces 86 to a planar anterior fixation surface 104 of the anterior flange 70. The anterior fixation surface 104 is opposite an anterior condyle surface 106, and, like the posterior fixation surfaces 82, the anterior fixation surface 104 extends generally in the superior/inferior direction.

The plurality of ribs 66 define a plurality of pockets 108 in each of the fixation surfaces 82, 86, 96, 100, and 104. In the illustrative embodiment, the pockets 108 are separated such that none of the pockets are in fluid communication with each other. It should be appreciated that in other embodiments two or more pockets may be in communication with one another such that a single, continuous pocket is formed in the fixation side 72 of the femoral trial 14. It will be appreciated that in other embodiments the pockets 108 may be omitted from one or more of the fixation surfaces.

The femoral trial 14 of the orthopaedic surgical instrument assembly 10 includes a plurality of teeth 110 that extend from each of the posterior fixation surfaces 82 in a direction away from the articular side 62. The teeth 110 are configured to engage or grip the surgically-prepared distal end of the patient's femur 20 when the femoral trial 14 is coupled thereto. The illustrative teeth 110 extend parallel to each other in the medial/lateral direction. It should be appreciated that in other embodiments the teeth 110 may be angled relative to each other or arranged in various patterns on the posterior fixation surfaces 82. Additionally, one or more of the teeth 110 may extend inferiorly/superiorly along the posterior fixation surface 82 in addition to, or instead of, extending medially/laterally as shown in FIGS. 3-4. It should also be appreciated that in other embodiments one or more teeth may be formed on any of the other surfaces 82, 86, 96, 100, and 104 of the fixation side 64 of the femoral trial 14.

As shown in FIG. 4, each tooth 110 has a triangular cross section when viewed in the sagittal plane. It should be appreciated that in other embodiments the teeth 110 may have a square cross section, rectangular cross section, dome-shaped cross section, or any other cross section suitable to engage the surgically-prepared distal end of the patient's femur 20. Additionally, while the teeth 110 have the same cross section in the illustrative embodiment, it should be appreciated that in other embodiments each tooth 110 may have a unique cross section.

Each tooth 110 has a body 112 including a base 114 fixed to the posterior fixation surface 82 between one or more of the pockets 108. The body 112 extends outwardly from the posterior fixation surface 82 to a tip 116. The tip 116 defines a longitudinal axis 122 of each tooth 110 extending in the medial/lateral direction. The tip 116 of each body 112 is spaced apart from the posterior fixation surface 82 such that each tooth 110 has a height 120. In the illustrative embodiment, the height 120 is approximately 0.38 millimeters. However, in other embodiments, the height 120 may be greater than that shown in the illustrative embodiment. Additionally, while each tooth 110 has the same height 120 in the illustrative embodiment, it should be appreciated that in other embodiments the height 120 of each tooth 110 may vary.

Figure 5:
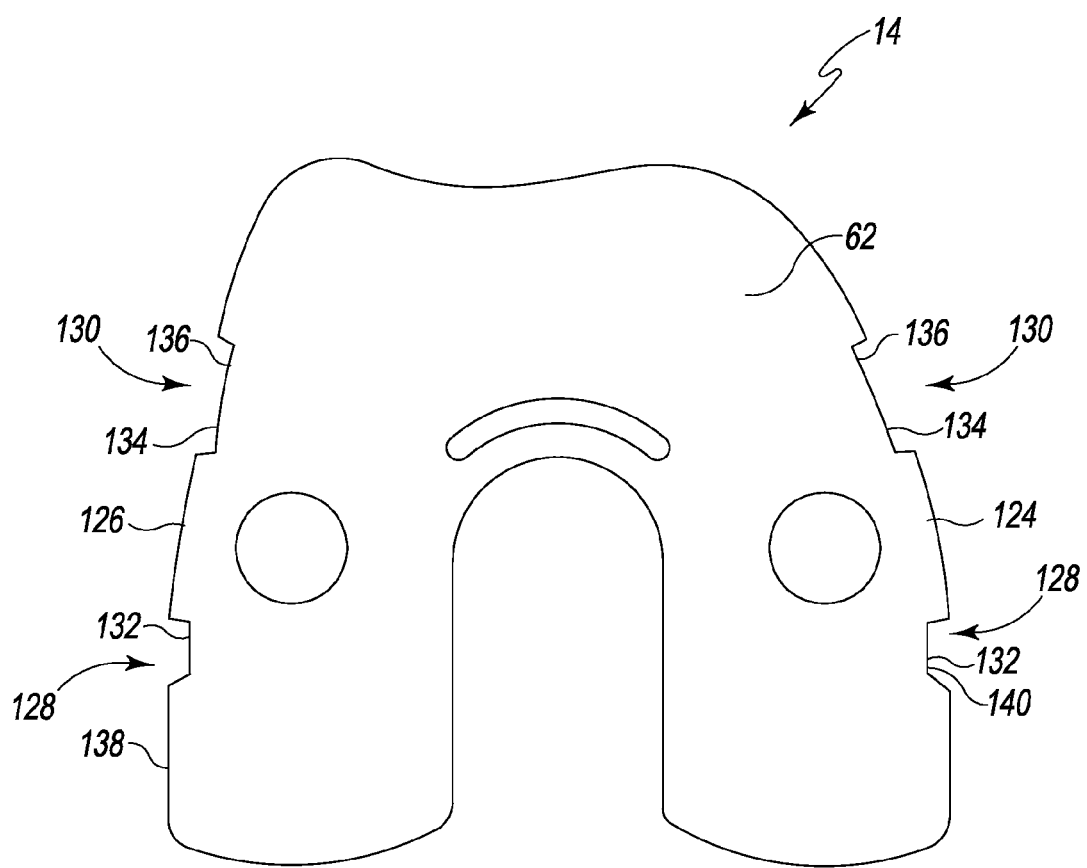
FIG. 5 is a bottom plan view of the femoral trial component of FIGS. 1-4.

The femoral trial 14 also includes a pair of sidewalls 124, 126 that extend between the articular side 62 and the fixation side 64, with one sidewall being medially positioned and the other laterally positioned depending on which knee is being replaced. As shown in FIG. 5, each of the sidewalls 124, 126 has a pair of notches 128, 130 defined therein. The notch 128 extends between the articular side 62 and the fixation side 64 of the distal condylar region 74 and has a base surface 132 that connects the distal fixation surface 86 to the distal condyle surface 88. Similarly, the notch 130 extends between the articular side 62 and the fixation side 64 of the distal condylar region 74 and the anterior-chamfer region 72. The notch 130 includes a base surface 134 that connects the distal fixation surface 86 to the distal condyle surface 88, and a base surface 136 that connects the anterior-chamfer fixation surface 100 and the anterior-chamfer condyle surface 102. In the illustrative embodiment, the notches 128, 130 extend inwardly approximately 1.75 millimeters from the sidewalls 124, 126, respectively, to the base surfaces 132, 134, 136.

The sidewalls 124, 126 define an outer edge 138 of the femoral trial 14 corresponding to a standard femoral prosthetic component size. The base surfaces 132, 134, 136 of the notches 128, 130 define another edge 140 of the femoral trial 14 corresponding to a standard, but more narrow, femoral prosthetic component size. As such, a single femoral trial 14 may be used to size multiple femoral prosthetic component sizes. It should be appreciated that in other embodiments one or more of the notches 128, 130 may be omitted from the femoral trial 14. It should also be appreciated that in other embodiments the position of the notches 128, 130 along the sidewalls 124, 126 may vary such that, for example, the notches 130 are formed entirely in the distal condylar region 74.

The femoral trial 14 is constructed from a polymeric material. In the illustrative embodiment, the polymeric material is a fifty percent glass-reinforced nylon. Another polymeric material that may be used is thirty percent glass-filled polyether ether ketone (PEEK) or polyethylene, such as ultrahigh molecular weight polyethylene (UHMWPE), although other biocompatible polymers may be used. The tibial bearing trial 18 may be constructed from a material, such as, for example, any of the polymeric materials described above, which permits smooth articulation between the tibial bearing trial 18 and the femoral trial 14. The tibial base trial 16 and the base insert 34 may be constructed from a biocompatible metal, such as a cobalt chrome alloy; other materials, such as ceramics, may also be used.

Figure 6:
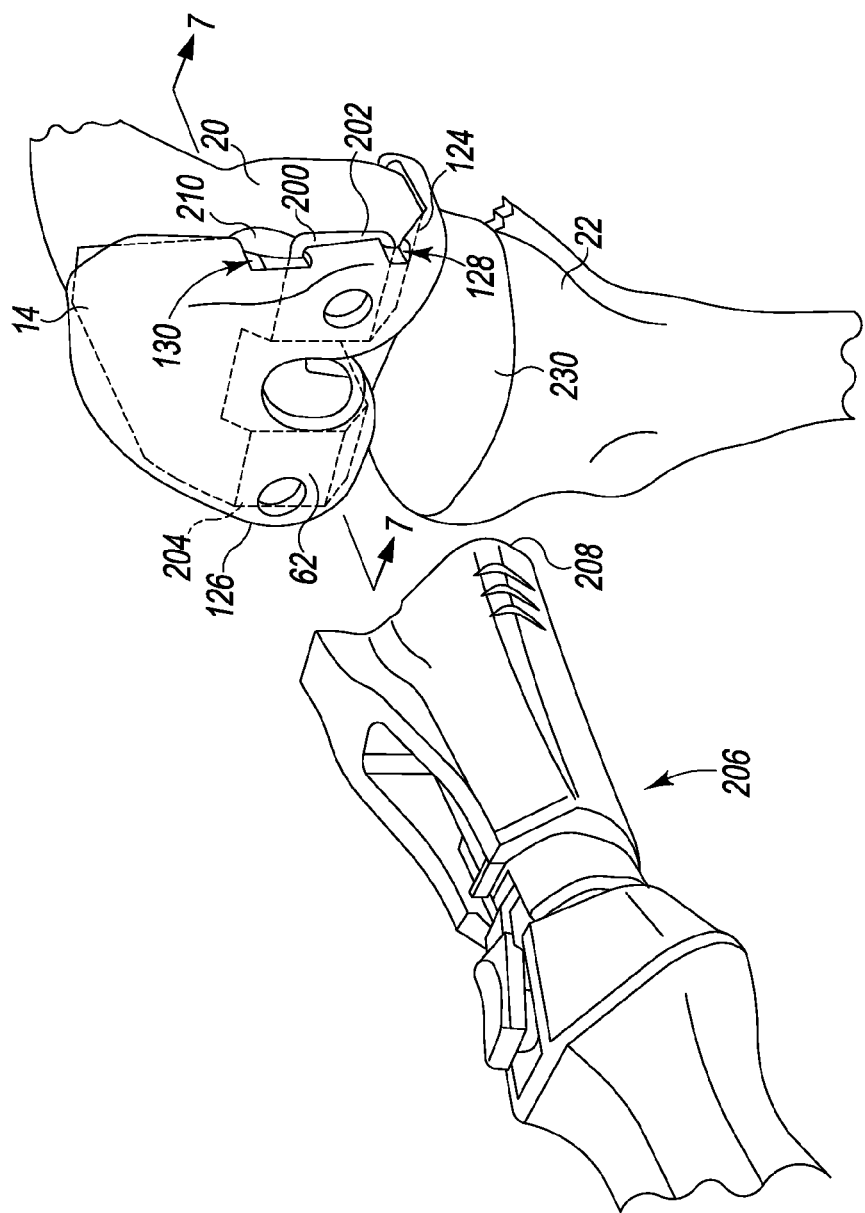
FIG. 6 is a perspective view of the femoral trial component of FIGS. 1-5 positioned on a surgically-prepared distal end of a patient's femur.

Referring now to FIGS. 6-9, the orthopaedic surgical instrument assembly 10 is shown in use with the patient's bony anatomy. As shown in FIG. 6, a surgically-prepared distal end 200 of the patient's femur 20 includes a resected medial condyle 202 and a resected lateral condyle 204. In use, the surgeon positions the femoral trial 14 over the distal end 200 of the patient's femur 20. An impactor assembly 206 may be used to impact the femoral trial 14 into the distal end 200.

To do so, an engagement end 208 of the impactor assembly 206 is positioned in contact with the articular side 62 of the femoral trial 14, and force is applied to the impactor assembly 206 until the fixation side 64 of the femoral trial 14 contacts the resected medial condyle 202 and the resected lateral condyle 204. Once the femoral trial 14 is properly positioned on the distal end 200 of the patient's femur 20, the surgeon may remove the impactor assembly 206. It should be appreciated that in other embodiments the surgeon may position the femoral trial 14 on the distal end 200 of the patient's femur 20 by hand without using the impactor assembly 206.

When the femoral trial 14 is positioned on the distal end 200 of the patient's femur 20, the sidewalls 124, 126 indicate where the outer edge of the standard femoral prosthetic component would be located on the resected medial condyle 202 and the resected lateral condyle 204. Conversely, the base surfaces 132, 134, 136 of the notches 128, 130 in the femoral trial 14 indicate where the outer edge of the narrow femoral prosthetic component would be located. If the sidewalls 124, 126 extend beyond the resected medial condyle 202 and the resected lateral condyle 204 of the distal end 200 of the patient's femur 20, the surgeon may select the narrow femoral prosthetic component for implantation.

Figure 7:
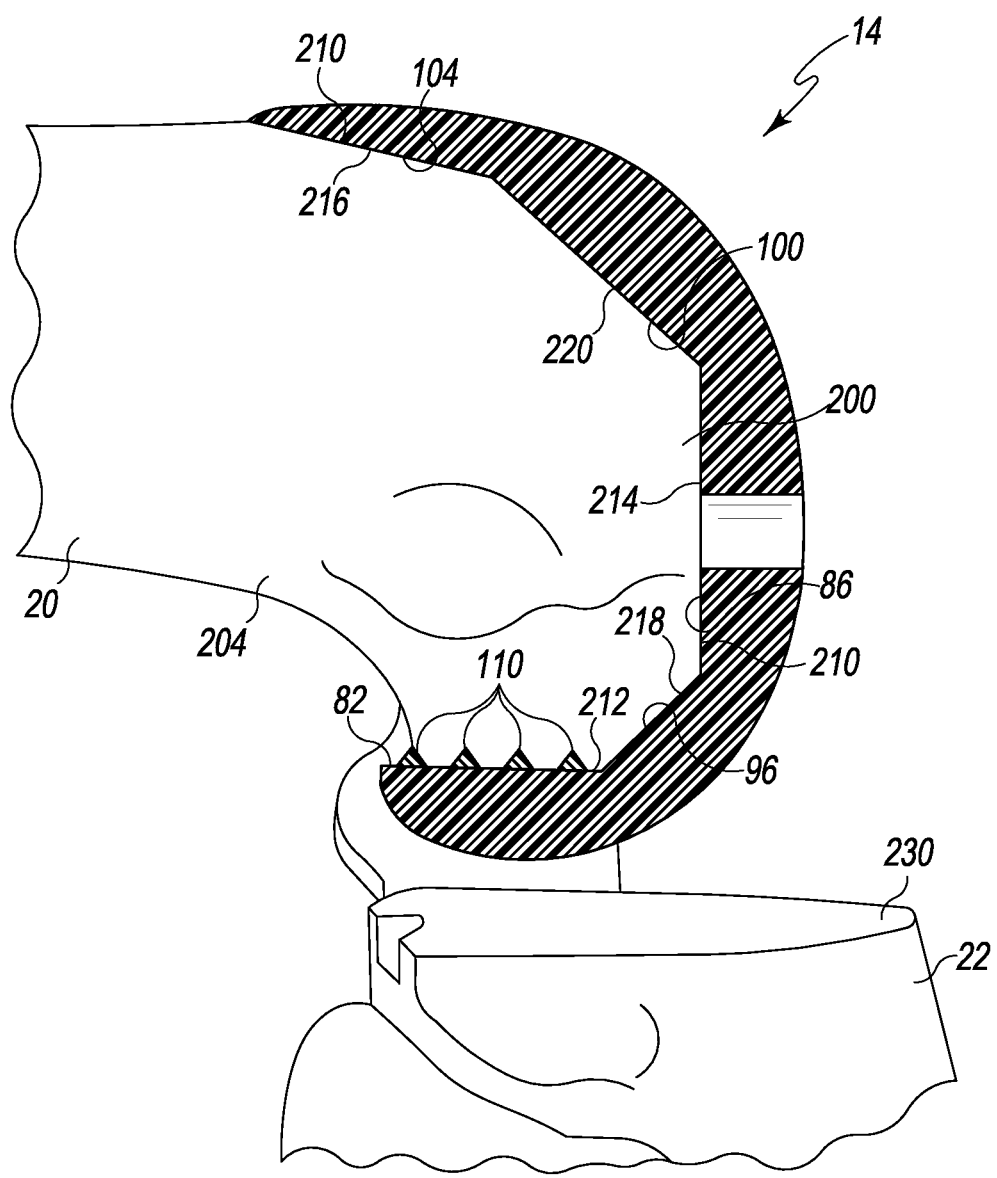
FIG. 7 is a sagittal cross sectional view of the femoral trial component of FIGS. 1-6 on the surgically-prepared distal end of the patient's femur.

The resected medial condyle 202 and the resected lateral condyle 204 of the patient's femur 20 include a number of resected surfaces 210. As shown in FIG. 7, the resected surfaces 210 of each condyle 202, 204 include a posterior planar surface 212, a distal planar surface 214, and an anterior planar surface 216. The resected surfaces 210 also include a posterior-chamfer planar surface 218 that extends superiorly and posteriorly from the distal planar surface 214 to the posterior planar surface 212 and an anterior-chamfer planar surface 220 that extends superiorly and anteriorly from the distal planar surface 214 to the anterior planar surface 216.

When the femoral trial 14 is positioned on the distal end 200 of the patient's femur 20, the anterior fixation surface 104 of the femoral trial 14 contacts the anterior planar surfaces 216 of the patient's femur 20 and the distal fixation surfaces 86 of the femoral trial 14 contacts the distal planar surfaces 214 of the patient's femur 20. Similarly, posterior-chamfer fixation surface 96 of the femoral trial 14 contacts the posterior-chamfer planar surface 218 of the patient's femur 20. The anterior-chamfer fixation surfaces 100 of the femoral trial 14 contacts the anterior-chamfer planar surfaces 220 of the patient's femur 20.

Further, the posterior fixation surfaces 82 of the femoral trial 14 grip the posterior planar surfaces 212 of the patient's femur 20 when the femoral trial 14 is positioned thereon. As shown in FIG. 7, one or more of the teeth 110 of the lateral posterior fixation surface 82 engages with, or grips, the posterior planar surface 212 of the resected lateral condyle 204. The engagement of the teeth 110 with the posterior planar surfaces 212 secures the femoral trial 14 to the distal end 200 of the patient's femur 20.

Figure 8:
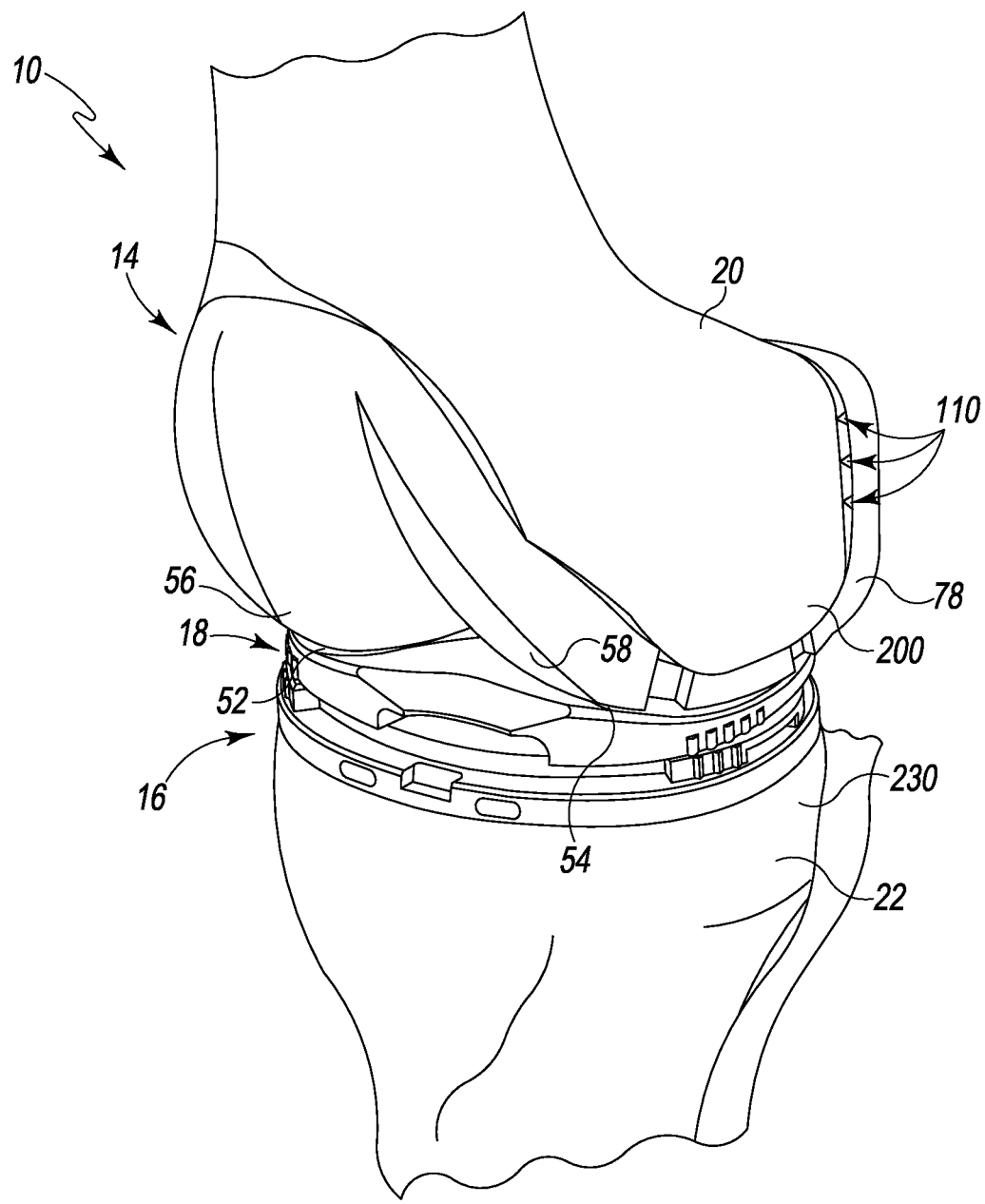
FIG. 8 is a perspective view of the orthopaedic surgical instrument assembly of FIG. 1 positioned on surgically-prepared ends of the patient's femur and tibia with the patient's knee in extension.

In addition to positioning the femoral trial 14 on the distal end 200 of the patient's femur 20, the surgeon may also position the tibial base trial 16 on a surgically-prepared proximal end 230 of the patient's tibia 22. When the surgical instrument assembly 10 is fully installed, the tibial base trial 16 is secured to the surgically-prepared proximal end 230 of the patient's tibia 22, as shown in FIG. 8. The tibial bearing trial 18, including the bearing surface trial 46 and the shim 48, are positioned over the post 42 of the base insert 34. The lateral condyle surface 56 of the femoral trial 14 contacts the lateral articular surface 52 of the tibial bearing trial 18, while the medial condyle surface 58 contacts the medial articular surface 54. The surgeon may then evaluate the range of motion and stability of the knee with the surgical instrument assembly 10.

Figure 9:
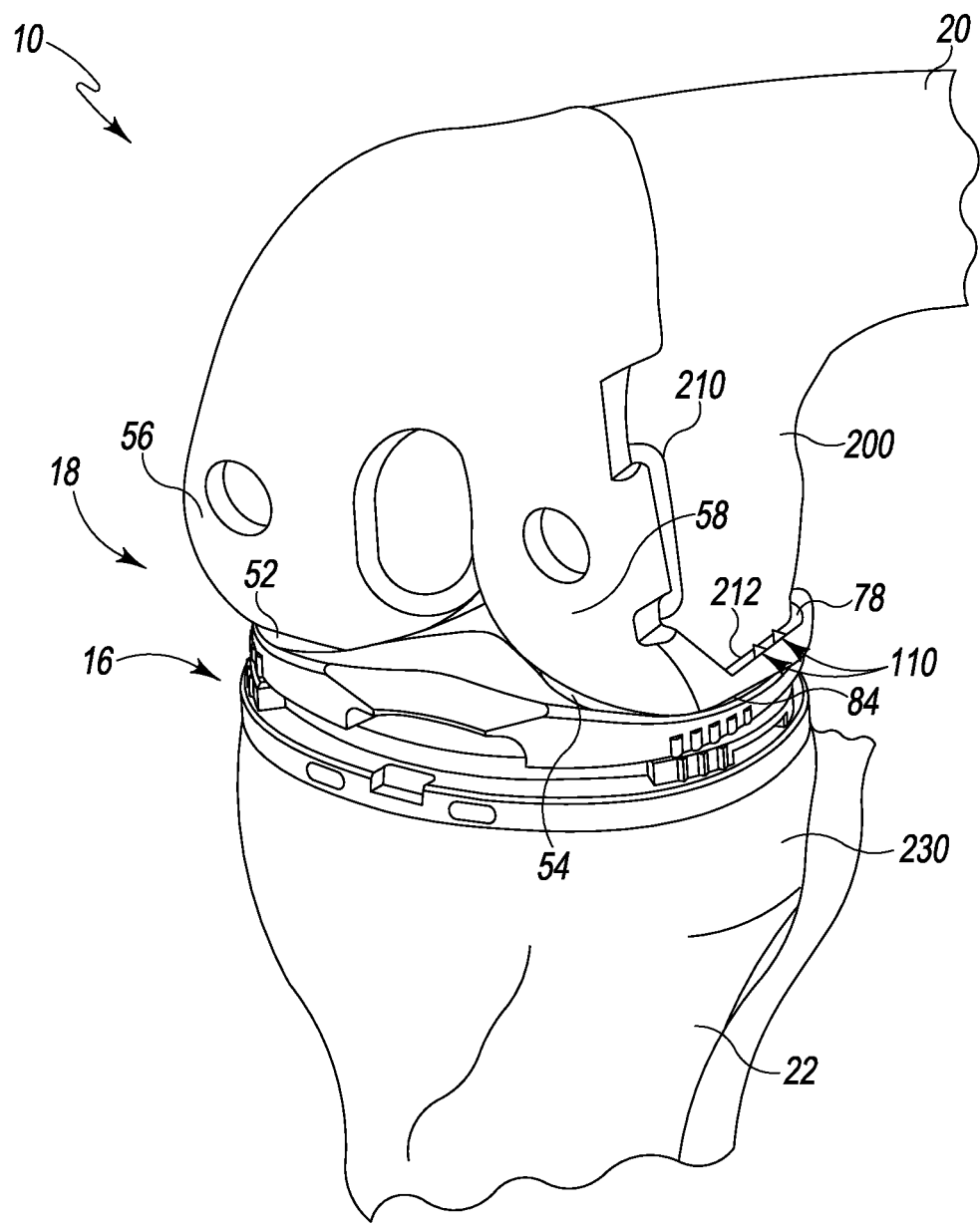
FIG. 9 is a perspective view of the orthopaedic surgical instrument assembly of FIG. 8 with the patient's knee in flexion.

As the range of motion is evaluated, the load on the femoral trial 14 translates posteriorly as the knee is moved from extension (see FIG. 8) to flexion (see FIG. 9). As the load moves posteriorly, the force normal to the posterior condyle surfaces 84 of the femoral trial 14 increases, thereby causing the teeth 110 of the posterior fixation surfaces 82 of the femoral trial 14 to further engage, or grip, the posterior planar surfaces 212 of the surgically-prepared distal end 200 of the patient's femur 20. The engagement of one or more of the teeth 110 of the femoral trial 14 with the distal end 200 of the patient's femur 20 retains the femoral trial 14 on the patient's femur 20. It should be appreciated that in other embodiments screws or other fasteners may be inserted through the through-holes 90 into the femur 20 to provide additional fixation.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of trialing prosthetic components of a knee prosthesis, the method comprising:

providing a first femoral prosthetic component having a first femoral prosthetic component size, providing a second femoral prosthetic component having a second femoral prosthetic component size different than the first femoral prosthetic component size, the second femoral component being more narrow than the first femoral prosthetic component, positioning a femoral trial component on a surgically-prepared distal end of a patient's femur, the femoral trial component comprising (i) an articular side comprising a femoral condyle surface having a curved contour corresponding with a curved contour of a femoral condyle surface of at least one of the femoral prosthetic components, (ii) a fixation side that is opposite the articular side, the fixation side comprising a fixation surface that engages the surgically-prepared distal end of the patient's femur, (iii) medial side including a first medial surface and a second medial surface that extend between the femoral condyle surface and the fixation surface, and (iv) a lateral side that is opposite the medial side, the lateral side including a first lateral surface and a second lateral surface that extend between the femoral condyle surface and the fixation surface, identifying a position of the first medial surface and the first lateral surface of the femoral trial component relative to an outer edge of the surgically-prepared distal end of the patient's femur, the first medial surface and the first lateral surface defining a first outer edge corresponding to the first femoral component size, identifying a position of the second medial surface and the second lateral surface of the femoral trial component relative to the outer edge of the surgically-prepared distal end of the patient's femur, the second medial surface and the second lateral surface defining a second outer edge corresponding to the second femoral component size, and selecting (i) the second femoral prosthetic component if any part of the first outer edge is positioned beyond the outer edge of the surgically-prepared distal end of the patient's femur and the second outer edge is positioned within the outer edge of the surgically-prepared distal end of the patient's femur, and (ii) the first femoral prosthetic component if the first outer edge of the femoral trial component is positioned within the outer edge of the surgically-prepared distal end of the patient's femur.

2. The method of claim 1, further comprising drilling a pair of fixation holes in the surgically-prepared distal end of the patient's femur.

3. The method of claim 2, wherein drilling the pair of fixation holes includes inserting a surgical drill into a guide hole defined in the femoral trial component.

4. The method of claim 1, wherein selecting the second femoral prosthetic component further comprises:

selecting the second femoral prosthetic component when the outer edge of the surgically-prepared distal end of the patient's femur is visible through a medial notch defined in the femoral trial component, the medial notch being defined by the second medial surface and a first pair of spaced surfaces extending between the first medial surface and the second medial surface, wherein the second medial surface extends between and connects the first pair of spaced surfaces.

5. The method of claim 1, wherein selecting second femoral prosthetic component further comprises:

selecting the second femoral prosthetic component when the outer edge of the surgically-prepared distal end of the patient's femur is visible through a lateral notch defined in the femoral trial component, the lateral notch being defined by the second lateral surface a second pair of spaced surfaces extending between the first lateral surface and the second lateral surface, wherein the second lateral surface extends between and connects the second pair of spaced surfaces.

6. The method of claim 1, wherein selecting the first femoral prosthetic component further comprises selecting the first femoral prosthetic component if a medial-lateral dimension of the surgically-prepared distal end of the patient's femur defined between a lateral-most point and a medial-most point of the outer edge of the surgically-prepared distal end of the patient's femur is greater than a first medial-lateral dimension of the femoral trial component defined between the first medial surface and the first a lateral surface, the first medial-lateral dimension matching a medial-lateral dimension of the first femoral prosthetic component.

7. The method of claim 6, wherein selecting the second femoral prosthetic component further comprises selecting the second femoral prosthetic component if the medial lateral dimension of the surgically-prepared distal end of the patient's femur is less than the first medial-lateral dimension of the femoral trial component and is greater than a second medial-lateral dimension defined between the second medial surface and the second lateral surface, the second medial-lateral dimension matching a medial-lateral dimension of the second femoral prosthetic component.

8. A method of trialing prosthetic components of a knee prosthesis, the method comprising:

providing a first femoral prosthetic component having a first femoral prosthetic component size, providing a second femoral prosthetic component having a second femoral prosthetic component size that is less than the first femoral prosthetic component size, positioning a femoral trial component on a surgically-prepared distal end of a patient's femur such that a fixation surface of the femoral trial component engages with the surgically-prepared distal end of the patient's femur, the femoral trial component further comprising: (i) a medial side including a first medial surface and a second medial surface that extend distally from the fixation surface, and (ii) a lateral side positioned opposite the medial side, the lateral side including a first lateral surface and a second lateral surface that extend distally from the fixation surface, identifying a position of the first medial surface and the first lateral surface of the femoral trial component relative to an outer edge of the surgically-prepared distal end of the patient's femur, and selecting (i) the first femoral prosthetic component if the first medial surface and the first lateral surface of the femoral trial component are positioned within the outer edge of the surgically-prepared distal end of the patient's femur, and (ii) the second femoral prosthetic component if any part of the first medial surface or the first lateral surface is positioned beyond the outer edge of the surgically-prepared distal end of the patient's femur.

9. The method of claim 8, further comprising identifying a position of the second medial surface and the second lateral surface of the femoral trial component relative to the outer edge of the surgically-prepared distal end of the patient's femur.

10. The method of claim 9, wherein selecting the second femoral component further comprises selecting the femoral component if the second medial surface and the second lateral surface are positioned within the outer edge of the surgically-prepared distal end of the patient's femur.

11. The method of claim 8, further comprising drilling a pair of fixation holes in the surgically-prepared distal end of the patient's femur.

12. The method of claim 11, wherein drilling the pair of fixation holes includes inserting a surgical drill into a guide hole defined in the femoral trial component.

13. The method of claim 8, wherein selecting the second femoral prosthetic component further comprises selecting the second femoral prosthetic component when the outer edge of the surgically-prepared distal end of the patient's femur is visible through a medial notch and a lateral notch defined in the femoral trial component, the medial notch being defined by the second medial surface and a first pair of spaced surfaces extending between the first medial surface and the second medial surface, and the lateral notch being defined by the second lateral surface a second pair of spaced surfaces extending between the first lateral surface and the second lateral surface.

14. The method of claim 8, wherein selecting the first femoral prosthetic component further comprises selecting the first femoral prosthetic component if a medial-lateral dimension of the surgically-prepared distal end of the patient's femur defined between a lateral-most point and a medial-most point of the outer edge of the surgically-prepared distal end of the patient's femur is greater than a first medial-lateral dimension of the femoral trial component defined between the first medial surface and the first a lateral surface, the first medial-lateral dimension matching a medial-lateral dimension of the first femoral prosthetic component.

15. The method of claim 14, wherein selecting the second femoral prosthetic component further comprises selecting the second femoral prosthetic component if the medial lateral dimension of the surgically-prepared distal end of the patient's femur is less than the first medial-lateral dimension of the femoral trial component and is greater than a second medial-lateral dimension defined between the second medial surface and the second lateral surface, the second medial-lateral dimension matching a medial-lateral dimension of the second femoral prosthetic component.

* * * * *